United States Patent [19]

Ando

[11] Patent Number: 5,755,220
[45] Date of Patent: May 26, 1998

[54] FLOW ADJUSTING VALVE FOR ANESTHETIC DEVICE

[76] Inventor: Toshiharu Ando, 7-13, Nishikata 2-chome, Bunkyo-ku, Tokyo, Japan

[21] Appl. No.: 648,674

[22] Filed: May 16, 1996

[30] Foreign Application Priority Data

Feb. 9, 1996 [JP] Japan .................................... 8-023998

[51] Int. Cl.$^6$ ................................................. A61M 15/00
[52] U.S. Cl. ................ 128/203.12; 128/205.11; 128/205.24; 128/203.25
[58] Field of Search .................. 128/205.11, 205.24, 128/203.12, 203.25

[56] References Cited

FOREIGN PATENT DOCUMENTS

| | | |
|---|---|---|
| 58-50742 | 11/1983 | Japan . |
| 62-45713 | 12/1987 | Japan . |
| 7-1948 | 1/1995 | Japan . |
| 2136703 | 9/1984 | United Kingdom . |
| 2254258 | 10/1992 | United Kingdom . |

*Primary Examiner*—Aaron J. Lewis
*Attorney, Agent, or Firm*—Nikaido, Marmelstein, Murray & Oram LLP

[57] ABSTRACT

A flow adjusting valve for an anesthetic device has adjusting valves for an anesthetic gas other than oxygen, as well as for oxygen, respectively, both being contained in a valve main body. The valve main body has first and second valve seat chambers, first and second stopper edges, and first and second valve chambers arranged in the described order from an inlet side for respective adjusting valves. A bypass of restricted flow amount is provided in the oxygen adjusting valve. It has an inlet which opens into an inside on an upstream side of the second valve seat chamber and which communicates with a discharge passage through the valve main body. First and second movable valve seats with first and second central valve openings are slidably contained in the valve seat chambers and are pushed by first and second springs against the stopper edges. First and second valve members are arranged inside the first and second valve chambers such that the movable valve seats are moved towards the inlet side against the springs after the central valve openings have been closed. The inlet of the bypass is thus closed when the second movable valve seat is moved towards the inlet side, and is opened when moved in the opposite direction.

6 Claims, 5 Drawing Sheets

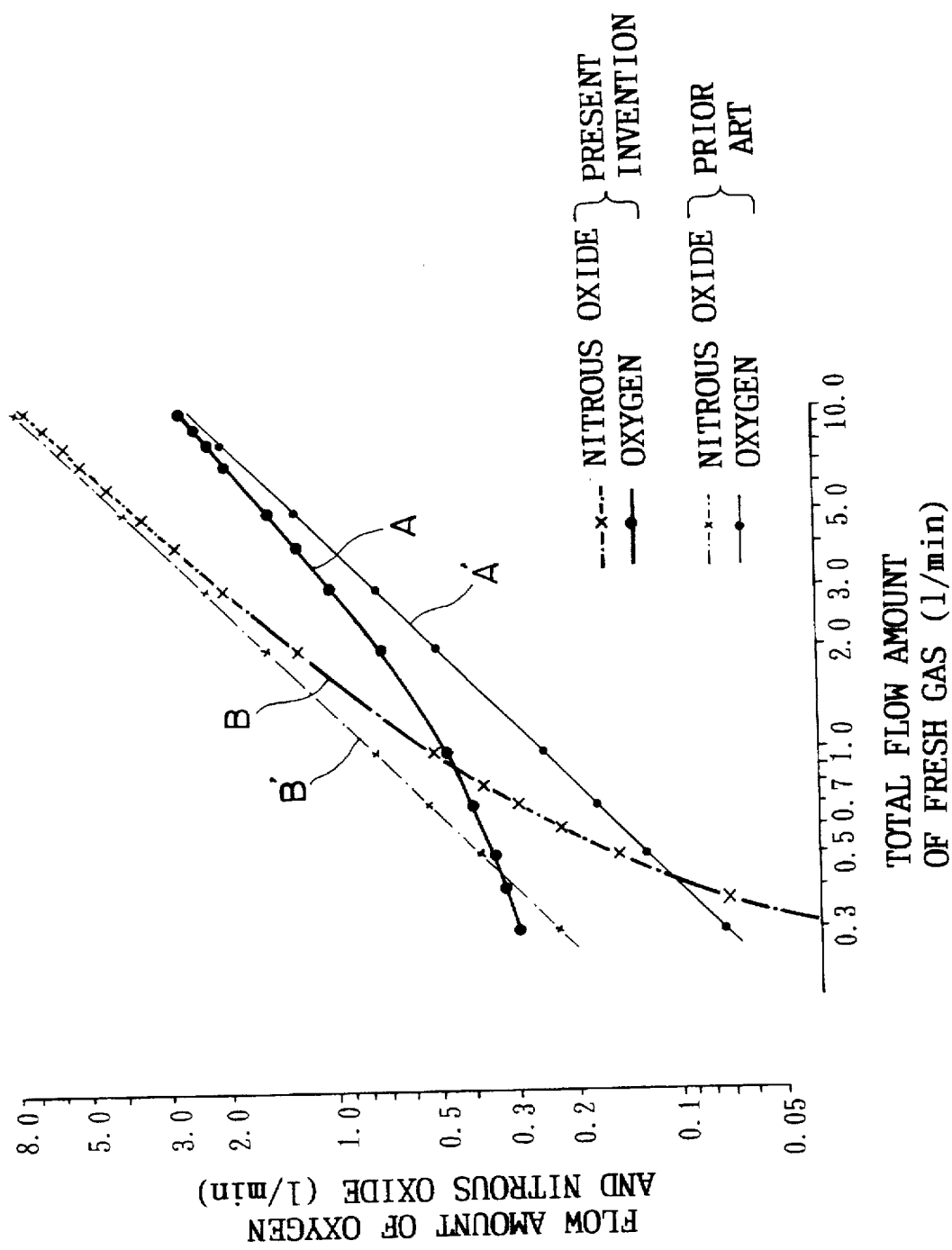

FLOW ADJUSTING VALVE FOR ANESTHETIC DEVICE

BACKGROUND OF THE INVENTION

1. Field of the Invention

The present invention relates to a flow adjusting valve for an anesthetic device which supplies a respiratory circuit of a patient with a fresh gas by mixing oxygen ($O_2$) and a gas (or gases) other than oxygen, i.e., by mixing oxygen and a gas (or gases) such as laughing gas (nitrous oxide, $N_2O$) or the like.

2. Description of the Related Art

The fresh gas for an anesthetic purpose is obtained by mixing oxygen and a gas (or gases) other than oxygen in a ratio, e.g., of 1:3 and is supplied to a respiratory circuit which passes through a mask of a patient. The amount of supply of the fresh gas is adjusted depending on the degree of anesthesia required. Inside the body of the patient oxygen is consumed in the amount of 200–300 ml/min to maintain the life of the patient. It follows that, when the patient is subjected to an anesthesia with a smaller flow amount of anesthetic agent or gas, an absolute amount of oxygen will become short if the amount of fresh gas is kept at around 300 ml/min. In addition, since the viscosity of oxygen is higher than that of nitrous oxide, oxygen is likely to be influenced by throttling of the flow amount. In this respect, too, the amount of oxygen is likely to become short.

FIG. 5 is a graph showing a mixing ratio of gases in which the abscissa represents a total flow amount of fresh gas and the ordinate represents a flow amount of oxygen and nitrous oxide. In the graph, curves A' and B' represent the amount of oxygen and nitrous oxide, respectively, at a substantially constant mixing ratio. Curves A and B represent an example of supply amount of oxygen and nitrous oxide according to the present invention.

In FIG. 5, when the total flow amount of fresh gas is set to be 300 ml/min, the amount of oxygen as represented by curve A' becomes 75 ml/min and the amount of nitrous oxide becomes 225 ml/min. The amount of oxygen becomes remarkably smaller than 200–300 ml/min that is required by the patient. In curves A and B, however, the amount of oxygen is 300 ml/min and the amount of nitrous oxide is 0 ml/min, with the result that no shortage of oxygen occurs. By increasing the total flow amount from this condition, the amount of nitrous oxide is rapidly increased while oxygen is gradually increased, to thereby attain a predetermined ratio. Therefore, in the flow amount adjusting apparatus for the anesthetic device, while an oxygen adjusting valve and a nitrous oxide adjusting valve (i.e., gas adjusting valve) are interlocked with each other, the oxygen adjusting valve is arranged to be adjustable independently without interlocking relationship with the other. The ratio of oxygen at the time of low degree of (or weak) anesthesia can thus be made larger.

In the invention by the present applicant as disclosed in Japanese Published Unexamined Utility Model Registration Application No. 1948/1995, there was provided a mechanism in which oxygen can be adjusted independently. There was also provided a bypass in a movable valve seat of an oxygen adjusting valve so that the amount of oxygen supply can be automatically increased by opening the bypass when the supply amount of fresh gas is small.

In the above-described invention, however, there are the following disadvantages. Namely, since the position in which the bypass is provided lies inside the very small movable valve seat, the machining of the bypass is difficult, and the amount of bypass cannot be adjusted.

SUMMARY OF THE INVENTION

In view of the above-described disadvantages, the present invention has an object of providing a flow adjusting valve for an anesthetic device in which oxygen can be automatically increased at the time of low flow amount of the fresh gas, and in which the bypass for increasing the amount of oxygen can be easily made. It has also an object of obtaining a mechanism in which the adjustment in the flow amount of oxygen passing through the bypass can be made easily.

In order to attain the above objects, the present invention is a flow adjusting valve for an anesthetic device comprising: a valve main body; a gas adjusting valve for adjusting an anesthetic gas other than oxygen and having a first valve member; an oxygen adjusting valve having a second valve member; both the adjusting valves being contained in the valve main body to supply the anesthetic gas and oxygen in a predetermined ratio by moving back and forth the first and second valve members; the valve main body having in respective portions corresponding to the respective adjusting valves: first and second valve seat chambers; first and second stopper edges; and first and second valve chambers, all being arranged in an order described from an inlet side of the adjusting valves; a bypass of restricted flow amount provided in the oxygen adjusting valve, the bypass having an inlet which opens into an inside on an upstream side of the second valve seat chamber and which communicates with a discharge passage through the valve main body; first and second movable valve seats both respectively being slidably contained in the first and second valve chambers and having first and second central valve openings, both the valve seats respectively being pushed by first and second springs towards the first and second stopper edges; and means for moving the first and second valve members which are disposed inside the first and second valve chambers such that the first and second movable valve seats are respectively moved towards the inlet side against the first and second springs after the first and second central valve openings have been closed by the first and second valve members, whereby the inlet of the bypass is closed by the movement of second movable valve seat towards the inlet side and is opened by the movement of the second movable valve seat in the opposite direction.

According to the above arrangement, the bypass for oxygen can be disposed inside the valve main body instead of in the movable valve seat. Therefore, the freedom of design of the bypass is improved and the manufacturing thereof becomes easier.

Preferably, the flow adjusting valve for an anesthetic device further comprises a bypass adjusting valve provided in the bypass, an adjusting section of the bypass adjusting valve being disposed outside the valve main body.

In this arrangement, the bypass adjusting valve for oxygen can be easily adjusted from an outside of the valve main body.

Preferably, the means for moving the first and second valve members comprises first and second knobs for respectively moving back and forth the first and second valve members into and out of engagement with the central valve openings; and a mechanism for interconnecting the operations of the first and second knobs.

In a preferred embodiment, the mechanism for interconnecting the operations of the first and second knobs is arranged to be selectively operated.

Preferably, the mechanism for selectively interconnecting the first and second knob comprises: a first gear fixedly mounted on the first valve member; a second gear loosely mounted on the second valve member; and an intermediate gear for meshing with both the first and second gears; the second gear and the second knob having a dog clutch mechanism so arranged that both are engaged in one direction of rotation of the first knob and are disengaged in the opposite direction of rotation thereof.

Still preferably, the mechanism for selectively interconnecting the first and second knob comprises: a first gear fixedly mounted on the first valve member; a second gear loosely mounted on the second valve member; and an intermediate gear for meshing with both the first and second gears; the second gear and the second knob having a dog clutch mechanism so arranged that both are engaged in one direction of rotation of the second knob and are disengaged in the opposite direction of rotation thereof.

BRIEF DESCRIPTION OF THE DRAWINGS

The above and other objects and the attendant advantages of the present invention will become readily apparent by reference to the following detailed description when considered in conjunction with the accompanying drawings wherein:

FIG. 5 is a diagram showing the operation of the flow adjusting valve.

DETAILED DESCRIPTION OF PREFERRED EMBODIMENTS

An explanation will now be made about preferred embodiments of the present invention with reference to the accompanying drawings.

Figure 1:
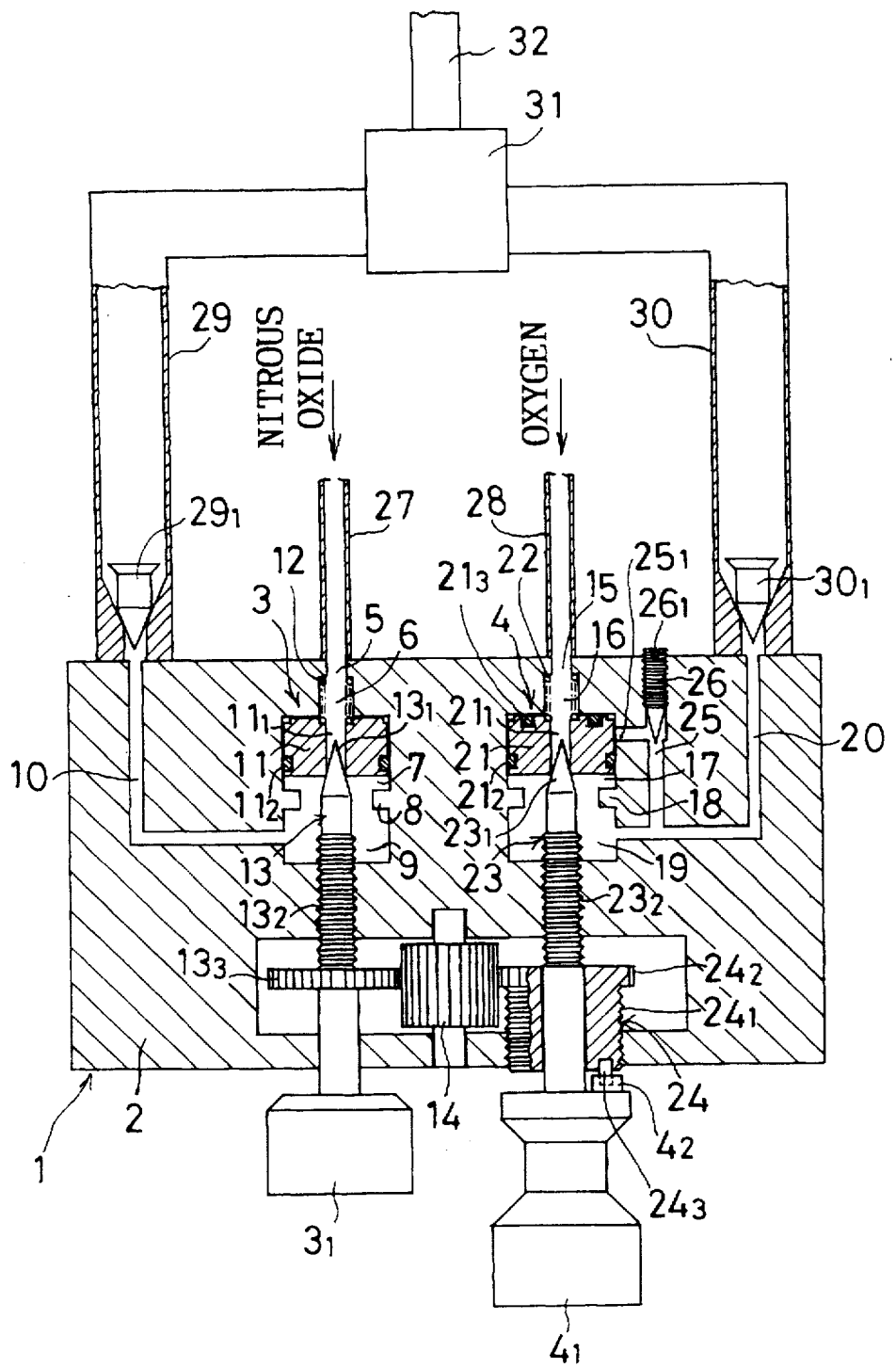
FIG. 1 is a sectional view showing one example of a flow adjusting valve, when closed, for an anesthetic device according to the present invention.

In FIG. 1, reference numeral 1 denotes a flow adjusting valve for mixing oxygen ($O_2$) and a laughing gas (nitrous oxide, $N_2O$). Reference numeral 2 denotes a valve main body. In this valve main body 2 there are provided a nitrous oxide adjusting valve (also called a gas adjusting valve) 3 and an oxygen adjusting valve 4. Both adjusting valves 3, 4 are operated by knobs $3_1$, $4_1$. The valve main body 2 is illustrated as an integral block for convenience' sale. However, it is actually formed by combining a plurality of members divided along suitable planes so as to dispose therein cavities, passages, or the like.

The gas adjusting valve 3 is provided in the order mentioned from a front end ("front" in this specification means an upper side as seen in FIG. 1) rearwards with an inlet 5, a spring chamber 6, a valve seat chamber 7, a stopper edge 8 and a valve chamber 9. The valve chamber 9 is communicated with an outside of the valve main body 2 by means of an outlet (or discharge) passage 10. Inside the valve seat chamber 7 there is slidably inserted a movable valve seat 11. This movable valve seat 11 has a perforated valve opening $11_1$ the center thereof (also called a central valve opening $11_1$). By means of an O-ring $11_2$ which is fitted onto a peripheral groove, airtightness between the movable valve seat 11 and the inner surface of the valve seat chamber 7 can be secured. The movable valve seat 11 is urged or pushed by a spring 12 against the stopper edge 8.

A valve member (or a valve element) 13 is disposed through the valve chamber 9 in such a manner as to lie opposite to the central valve opening $11_1$, and has a needle portion $13_1$ for adjusting the flow amount, a threaded portion $13_2$ and a gear $13_3$ which is for interlocking operation. The threaded portion $13_2$ is screwed into a female thread in the valve main body 2 and therefore moves back and forth by the rotation of the knob $3_1$ which is integral therewith. The gear $13_3$ is in mesh with a long intermediate gear 14.

The oxygen adjusting valve 4 is also provided in the order mentioned from a front end rearwards with an inlet 15, a spring chamber 16, a valve seat chamber 17, a stopper edge 18 and a valve chamber 19. The valve chamber 19 is communicated with an outside of the valve main body 2 by means of an outlet (or discharge) passage 20. Inside the valve seat chamber 17 there is slidably inserted a movable valve seat 21. This movable valve seat 21 is urged by a spring 22 and has a perforated valve opening $21_1$ in the center thereof (also called a central valve opening $21_1$). By means of an O-ring $21_2$ which is fitted onto a peripheral groove, airtightness between the movable valve seat 21 and the inner surface of the valve seat chamber 17 can be secured. By means of an O-ring $21_3$ which is fitted onto a ring groove in a front end surface, the movable valve seat 21 is arranged to be in airtight contact, when moved forward, with the front end surface of the valve seat chamber 17.

A valve member (or a valve element) 23 has a needle portion $23_1$ for adjusting the flow amount and a threaded portion $23_2$. This threaded portion $23_2$ is threaded into a female thread in the valve main body 2. A cylindrical thread 24 is threaded into the valve main body 2 in a condition in which the cylindrical thread 24 is loosely mounted on the valve member 23. A gear $24_2$ which is integral with the cylindrical thread 24 is engaged with the intermediate gear 14. The gears $13_3$, $24_2$ have the same diameters and the threaded portions $13_2$, $23_2$, $24_1$ have the same pitch.

Further, on the rear (i.e., bottom in FIG. 1) surface of the cylindrical thread 24, there is provided a projection $24_3$ in a rearwardly projecting manner. On the front surface of the knob $4_1$, there is provided a projection $4_2$ in a forwardly projecting manner. The latter projection $4_2$ is arranged to be engaged with the former projection $24_3$ by a height equivalent to one pitch of the thread. The projections $4_2$ and $24_3$ constitute a dog clutch mechanism (or a latching mechanism.)

The mechanism for operating the valve by these gears and the thread is the same as the one shown in the above-described prior art. Namely, when the knob $3_1$ for the gas adjusting valve 3 is rotated in the direction of opening the valve, the projections $24_3$, $4_2$ get engaged with each other. The knob $4_1$ of the oxygen adjusting valve 4 is thereby also rotated by the same angle, and the valve members 13, 23 move backwards by the corresponding distance to thereby open the valves. When the knob $3_1$ is rotated in the direction of closing the valve, the cylindrical thread 24 moves forwards and the engagement between the projections $24_3$, $4_2$ is released, whereby the valve member 23 is prevented from moving.

Figure 3:
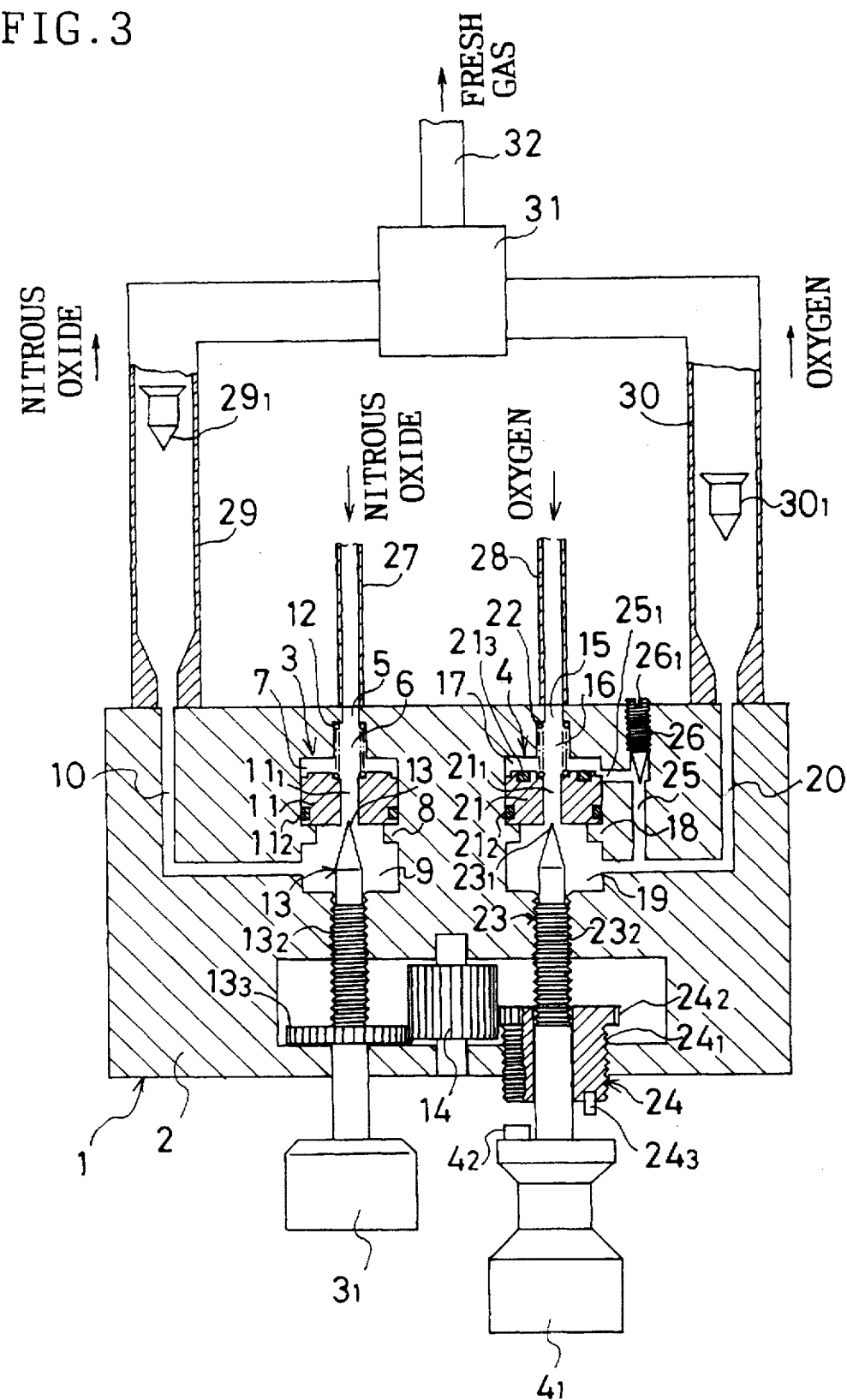
FIG. 3 is a sectional view thereof in a condition in which the bypass is opened.

In addition, when the knob $4_1$ for the oxygen adjusting valve 4 is rotated in the direction of closing it, the projections $24_3$, $4_2$ get engaged with each other. The valve member 13 of the gas adjusting valve 3 is also rotated in the direction of closing it. thereby moving forwards together. When the knob $4_1$ is rotated in the direction of opening it, the engagement between the projections $24_3$, $4_2$ is released as shown in FIG. 3. whereby only the valve member 23 moves backwards. Therefore, the oxygen adjusting valve 4 can be moved in the direction of opening it irrespective of the gas adjusting valve 3. with the result that the ratio of oxygen can be increased arbitrarily.

In the side surface on the front side of the valve seat chamber 17 of the oxygen adjusting valve 4, there is opened an inlet $25_1$ of a bypass 25 which communicates the valve seat chamber 17 with the outlet passage 20 in a restricted or limited flow amount. By moving backwards the movable valve seat 21 towards the stopper edge 18, the inlet $25_1$ is opened to bring the bypass 25 into communication with the inlet port 15. In an intermediate portion of the bypass 25 there is disposed in a threaded manner a needle valve type of bypass adjusting valve 26. At the front (i.e., upper) end of the bypass adjusting valve 26 there is provided a groove (or a notch) $26_1$ which serves as an adjusting section. By engaging a screw driver or an equivalent tool with the groove $26_1$ and rotating it, the amount of bypass can be adjusted.

In the Figures, reference numerals 27 and 28 denote inlet pipes for the nitrous oxide and oxygen, respectively. Reference numerals $29_1$ and $30_1$ denote floating type of flow meters, reference numeral 31 denotes a mixing portion, and reference numeral 32 denotes a discharge pipe leading to a respiratory circuit.

Figure 2:
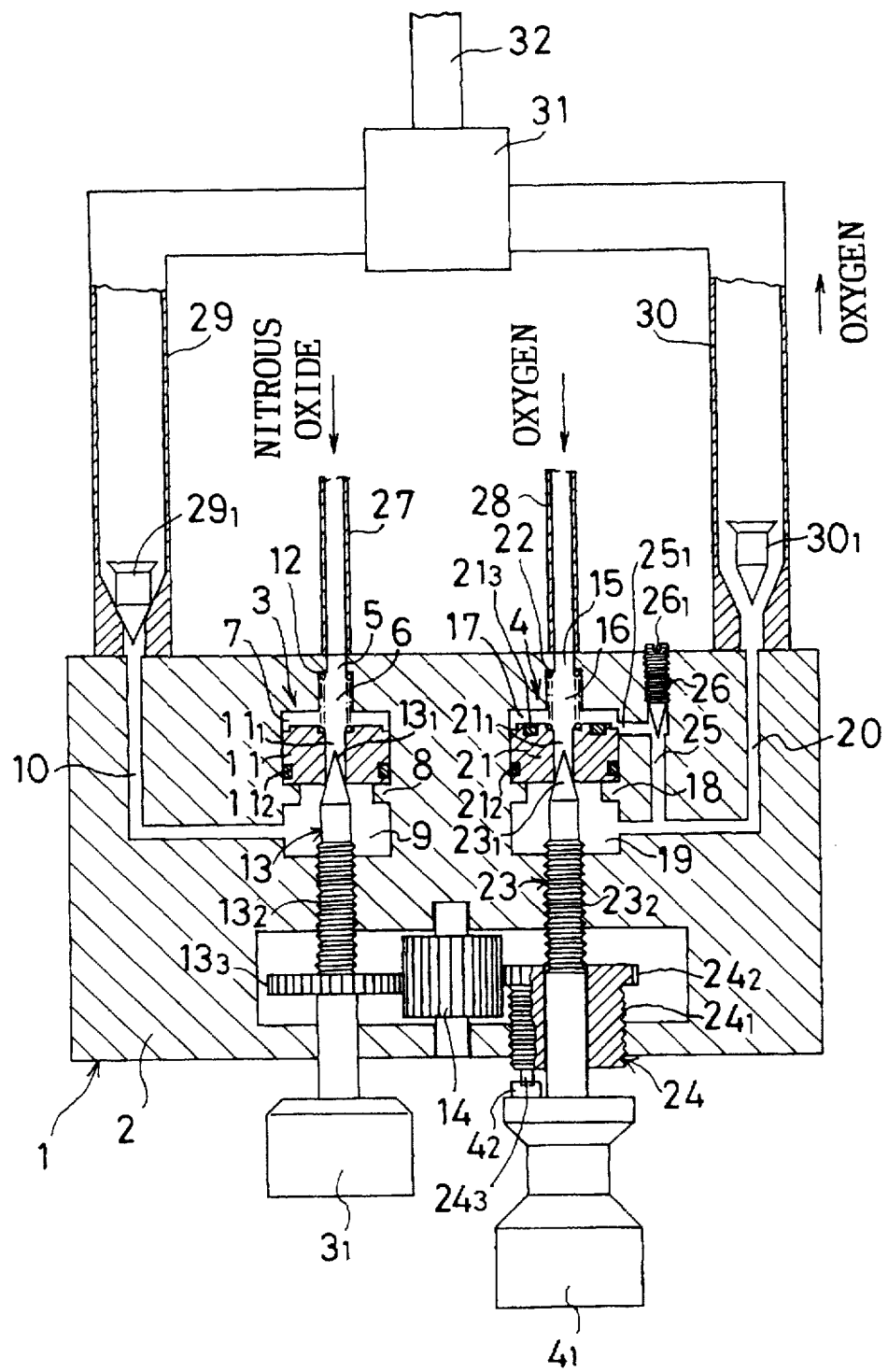
FIG. 2 is a sectional view thereof in a condition in which the bypass is at the beginning of opening.

Since the present invention has the above-described arrangement, the following operation can be made. Namely, when a fresh gas is to be sent out in the closed condition of the valves as shown in FIG. 1, the knob $3_1$ of the gas adjusting valve 3 is rotated in the direction of opening it. By the rotation of the knob $3_1$ the valve member 13 moves backwards as shown in FIG. 2. The cylindrical thread 24 also moves backwards (i.e., downwards in FIG. 1) at the same time while rotating, by the interlocking operation of the gears $13_3$, 14, $24_2$. The valve member 23 also rotates via the projections $24_3$, $4_2$ and moves backwards at the same time. As a result, the movable valve seats 11, 21 are pushed by the springs 12, 22 and moves backwards to follow the valve members 13, 23, thereby coming into abutment with the stopper edges 8, 18.

In this condition, the movable valve seat 21 of the oxygen adjusting valve 4 is away from the front surface of the valve seat chamber 17 to thereby open the inlet 15 to the valve seat chamber 17, and the inlet $25_1$ of the bypass 25 is opened to the valve seat chamber 17. Therefore, a small amount of oxygen flows out through the bypass 25 and the outlet passage 20, and is emitted from the discharge pipe 32 into the respiratory circuit of the patient.

If the knob $3_1$ is further rotated to thereby move backwards the valve members 13, 23 as shown in FIG. 3, the needle portions $13_1$, $23_1$ move away from the rear surfaces of the central valve openings $11_1$, $21_1$ in the movable valve seats 11, 21, thereby opening the valves. The nitrous oxide and oxygen thus flow out via the outlet passages 10, 20, get mixed in the mixing portion 31, and are supplied to the patient as a fresh gas from the discharge pipe 32. Each of the needle portions $13_1$, $23_1$ are arranged such that the flow amount can be adjusted while maintaining a predetermined ratio depending on the opening degree. However, the bypass 25 opens as described above prior to the opening of the valve members 13, 23, and a small amount of oxygen is supplied throughout the time before and during opening the valves.

Therefore, the smaller the amount of supply of the fresh gas is, the higher becomes the ratio of oxygen. The shortage of oxygen can thus be prevented even in case of application of a slight degree of (or weak) anesthesia.

The adjustment of oxygen through the bypass 25 can be performed by operating the bypass adjusting valve 26 while looking at the flow meter $29_1$ in the valve-closed condition as shown in FIG. 2.

When the valve member 13 of the gas adjusting valve 3 is moved forwards from a condition shown in FIG. 3 in the direction of closing it by rotating the knob $3_1$, the cylindrical thread 24 is rotated and the projection $24_3$ gets out of engagement with the projection $4_2$. The valve member 23 of the oxygen adjusting valve 4 will therefore be not rotated. When the valve member 23 is rotated in the direction of closing it by means of the knob $4_1$, the valve member 13 of the gas adjusting valve 3 also moves forwards in the direction of closing it by means of the projections $4_2$, $24_3$. However, when the knob $4_1$ is rotated in the direction of opening the valve, the projections $4_2$, $24_3$ get out of engagement with each other and only the valve member 23 moves backwards. This kind of arrangement is for the purpose of preventing the nitrous oxide from becoming too rich. However, as long as both the valve members 13, 23 are arranged to be capable of fine adjustment respectively, they may also be arranged to be normally moved in an integral manner.

Figure 4:
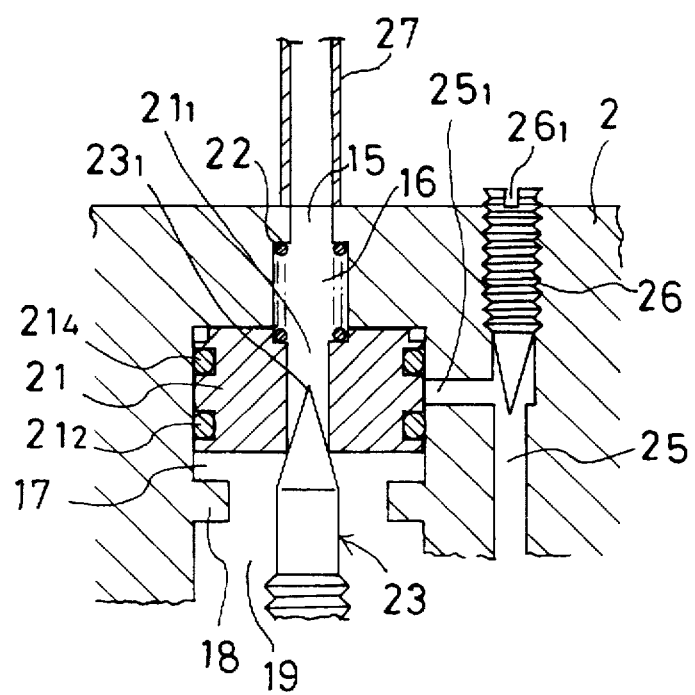
FIG. 4 is a sectional view of an important portion of another embodiment of the flow adjusting valve according to the present invention.

In the above-described embodiments, the O-ring $21_3$ is provided as a means of closing the bypass 25 when the valve members 13, 23 are moved forwards, such that the O-ring $21_3$ is closely adhered to the front surface of the valve seat chamber 17. However, as shown in FIG. 4, there may be provided an O-ring $21_4$ in the periphery of the front side of the movable valve seat 21 such that, when the movable valve seat 21 is moved backwards, the O-ring $21_4$ is positioned in the rear of (i.e., below) the opening $25_1$. It is also possible to provide suitable sealing means in place of the above-described O-rings.

According to the above arrangement, each of the movable valve seats of the gas adjusting valve and the oxygen adjusting valve is arranged to be movable, prior to their opening, by a predetermined distance together with each of the valve members. A bypass which allows for flowing of a restricted (or limited) amount of oxygen is provided between the valve seat chamber of the oxygen adjusting valve and the discharge passage. It is thus so arranged that the bypass is opened in the course of movement of the movable valve seat. An extra amount of oxygen can therefore be supplied by opening the bypass from an initial stage of opening the valves. It has consequently an effect in that the shortage of oxygen does not occur even at the time of weak anesthesia. In addition, since the bypass is disposed inside the valve main body, the freedom of design of the bypass is improved and the manufacturing thereof becomes easier, as compared with the one in which the bypass is provided inside the movable valve seat.

Further, since the bypass is provided with an adjusting valve such that it can be adjusted from outside the valve main body, it has an advantage in that the amount of oxygen can be finely adjusted.

It is readily apparent that the above-described flow adjusting valve for an anesthetic device meets all of the objects mentioned above and also has the advantage of wide commercial utility. It should be understood that the specific form of the invention hereinabove described is intended to be representative only, as certain modifications within the scope of these teachings will be apparent to those skilled in the art.

Accordingly, reference should be made to the following claims in determining the full scope of the invention.

What is claimed is:

1. A flow adjusting valve for an anesthetic device comprising:

a valve main body;

a gas adjusting valve for adjusting an anesthetic gas other than oxygen and having a first valve member;

an oxygen adjusting valve having a second valve member; both said adjusting valves being contained in said valve main body to supply the anesthetic gas and oxygen in a predetermined ratio by moving back and forth said first and second valve members;

said valve main body having in respective portions corresponding to said respective adjusting valves: first and second valve seat chambers; first and second stopper edges; and first and second valve chambers, all being arranged in an order described from an inlet side of said adjusting valves;

said valve main body having a bypass passage of restricted flow amount defined therethrough provided for said oxygen adjusting valve, said bypass passage having an inlet which opens into an inside on an upstream side of said second valve seat chamber and which communicates through said valve main body with a discharge passage;

first and second movable valve seats both respectively being slidably contained in said first and second valve chambers and having first and second central valve openings, both said valve seats respectively being pushed by first and second springs towards said first and second stopper edges; and means for moving said first and second valve members which are disposed inside said first and second valve chambers such that said first and second movable valve seats are respectively moved towards the inlet side against said first and second springs after said first and second central valve openings have been closed by said first and second valve members.

whereby the inlet of said bypass is closed by the movement of said second movable valve seat towards the inlet side and is opened by the movement of said second movable valve seat in the opposite direction.

2. A flow adjusting valve for an anesthetic device according to claim 1, further comprising a bypass adjusting valve provided in said bypass, an adjusting section of said bypass adjusting valve being disposed outside said valve main body.

3. A flow adjusting valve for an anesthetic device according to claim 1 or 2, wherein said means for moving said first and second valve members comprises:

first and second knobs for respectively moving back and forth said first and second valve members into and out of engagement with said central valve openings; and a mechanism for interconnecting the operations of said first and second knobs.

4. A flow adjusting valve for an anesthetic device according to claim 3, wherein said mechanism for interconnecting the operations of said first and second knobs is arranged to be selectively operated.

5. A flow adjusting valve for an anesthetic device according to claim 4, wherein said mechanism for selectively interconnecting said first and second knob comprises:

a first gear fixedly mounted on said first valve member;

a second gear loosely mounted on said second valve member; and an intermediate gear for meshing with both said first and second gears;

said second gear and said second knob having a dog clutch mechanism so arranged that both are engaged in one direction of rotation of said first knob and are disengaged in the opposite direction of rotation thereof.

6. A flow adjusting valve for an anesthetic device according to claim 4, wherein said mechanism for selectively interconnecting said first and second knob comprises:

a first gear fixedly mounted on said first valve member;

a second gear loosely mounted on said second valve member; and an intermediate gear for meshing with both said first and second gears;

said second gear and said second knob having a dog clutch mechanism so arranged that both are engaged in one direction of rotation of said second knob and are disengaged in the opposite direction of rotation thereof.

* * * * *